United States Patent [19]

Whipperman et al.

[11] 3,948,260
[45] Apr. 6, 1976

[54] CLOSURE MEANS FOR SYRINGE

[75] Inventors: Ronald Lee Whipperman, Gurnee Village; James Robert Gross, Bensenville Village, both of Ill.; Theodore Albert Miller, Jr., Ashland, Ohio

[73] Assignee: Abbott Laboratories, North Chicago, Ill.

[22] Filed: Nov. 4, 1974

[21] Appl. No.: 520,339

[52] U.S. Cl. .................................. 128/247; 128/251
[51] Int. Cl.² ............................................. A61M 3/00
[58] Field of Search .......... 128/247, 232, 251, 230, 128/239; 285/391, 360, 376, 401, 423; 85/47

[56] References Cited
UNITED STATES PATENTS

| | | | |
|---|---|---|---|
| 633,324 | 9/1899 | Luke | 285/391 X |
| 1,203,546 | 10/1916 | Parsons | 285/391 |
| 2,664,893 | 1/1954 | Kempel | 128/232 |
| 3,399,676 | 9/1968 | McLaughlin | 128/247 |
| 3,530,858 | 9/1970 | Edwards | 128/232 |
| 3,688,766 | 9/1972 | Kempel | 128/232 |

*Primary Examiner*—John D. Yasko
*Attorney, Agent, or Firm*—Robert L. Niblack; Neil E. Hamilton

[57] ABSTRACT

A closure means for a syringe of the type wherein the nozzle or stem is intended to be transported separately from the syringe body. Double, continuous threads are provided on the nozzle or stem to be engaged by two pairs of oppositely positioned wedges in a connecting member which are positioned in a helical pattern to accommodate the threads of the nozzle or stem, with one of the pairs of wedges positioned at a different flight on the helix than the other pair and all of the wedges positioned 90° from each other.

7 Claims, 6 Drawing Figures

U.S. Patent  April 6, 1976  3,948,260
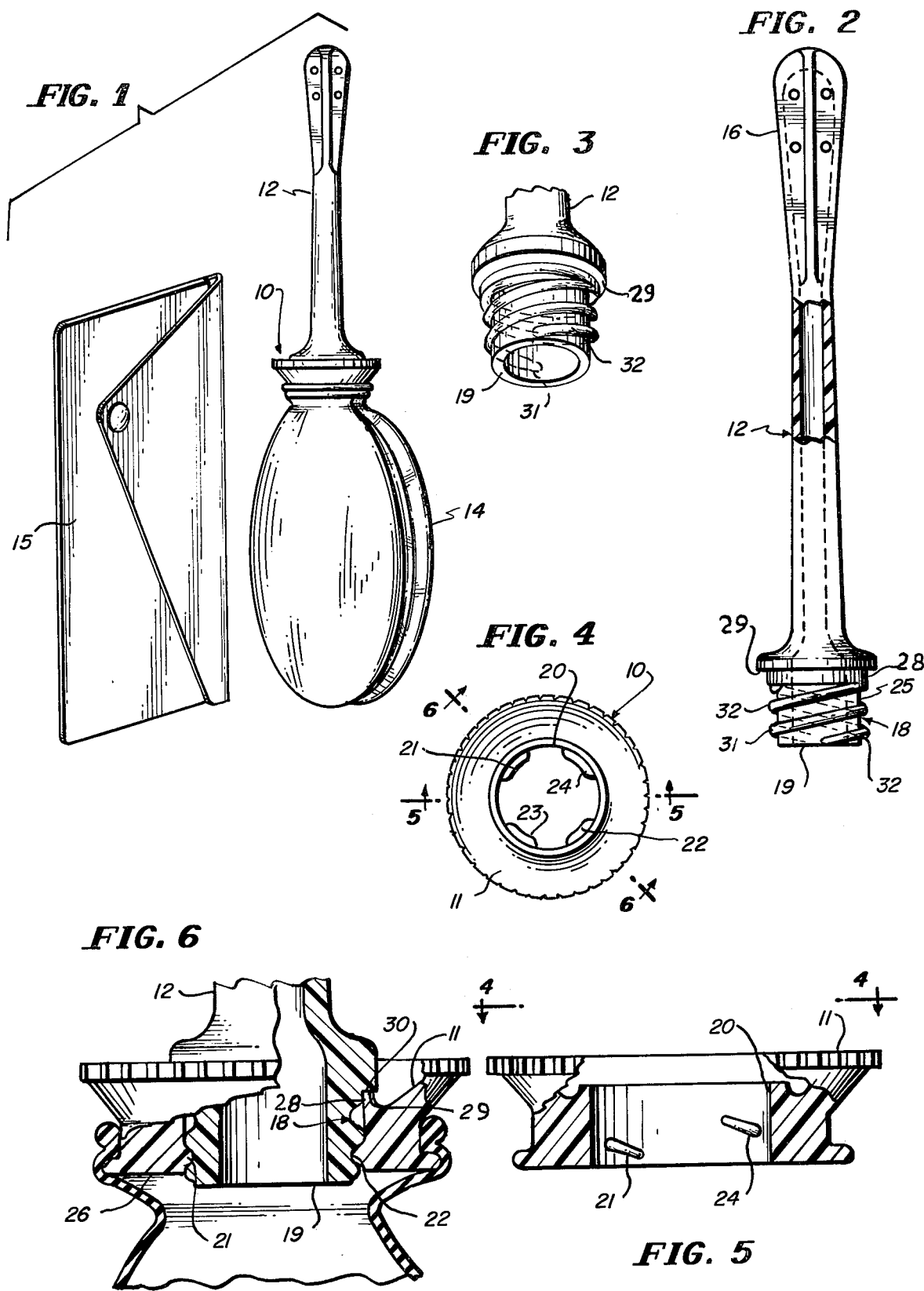

3,948,260

CLOSURE MEANS FOR SYRINGE

BACKGROUND OF THE INVENTION

This invention relates to a closure means for a syringe wherein a rapid and fluid-tight connection can be made between a nozzle or stem portion and the main body of the syringe. More particularly, this invention relates to a rapid closure connection for a disposable-type douche kit which can be easily transported when the nozzle member is removed.

Closure means for the types of syringes concerned with in this invention are described in U.S. Pat. No. 2,664,893 and U.S. Pat. No. 3,688,766. The main problem confronting the prior art in attempting to provide a connection between a removable nozzle or stem and a compressible bag which would contain a solution, is a fluid-tight connection. Another problem resides in the molding of the various threads or locking means in the hollow stem and the usual plug portion which is attached to the compressible bag. Ideally, the best means of securing two components of this type together for a temporary fluid-type fitment is a full thread on each component. However, this poses problems in molding in that such a threaded member must be turned to a large extent in order to remove it from a mold. Attempts in this direction to alleviate molding problems are shown in U.S. Pat. No. 2,664,893 where a bayonet-type threaded stem is disclosed. An attempt to simplify molding procedures as well as provide a fluid-type connection is described in U.S. Pat. No. 3,688,766 wherein a pair of semicircular helixes are disposed in a plug member with a complementary pair of helixes placed on the stem portion for interfitment and to draw the stem into sealing engagement with the plug. However, even with this latter arrangement, substantial turning of the stem must take place when the stem is fitted onto the plug and a fluid-tight seal is not always assured.

It is an advantage of the present invention to provide a novel closure means for a syringe which is intended to be disassembled for compactness and ease of travel. Other advantages include a disposable syringe wherein the stem member can be attached to the compressible bag in a quick and fluid-tight manner as well as affording a closure means which is easily molded.

SUMMARY OF THE INVENTION

The foregoing advantages are accomplished and the shortcomings of the prior art are overcome by the present closure means which is comprised of a nozzle or stem member which has a double threaded means disposed externally of and adjacent to the inlet of the hollow nozzle member. The double threaded means are defined by double threads composed of two oppositely positioned helixes having the same angle of inclination. A connecting member which encloses the end of a compressible bag for a solution, presents an annular inner surface wherein there are positioned two pairs of wedges disposed in a helical pattern and spaced at at least four different positions in the annular inner surface. The wedges have an arcuate length which exceeds no more than about 50% of the annular inner surface. This arrangement provides upon engagement of the wedges by the double threads a fast and secure connection with a minimum of effort and rotation as well as affording a unit which is easily molded. In a preferred manner, the pairs of wedges are located at a position 180° from each other with the second pair of wedges at a different flight than the first pair and all of the wedges spaced 90° apart.

BRIEF DESCRIPTION OF THE DRAWING

A better understanding of the present closure means will be accomplished by reference to the drawing wherein:

FIG. 1 is a view in side elevation showing an assembled syringe unit with an envelope-type carrying case for housing the unit when the stem is detached.

FIG. 2 is a view in side elevation with portions broken away illustrating the stem portion with a double helix thread.

FIG. 3 is a partial perspective view of the stem portion shown in FIG. 2 showing the double threaded end portion.

FIG. 4 is a top view taken along line 4—4 of FIG. 5 illustrating the positioning of the four inner wedges.

FIG. 5 is a view in vertical section taken along line 5—5 of FIG. 4 and illustrating the positioning of two of the wedges at different flights.

FIG. 6 is a view taken along line 6—6 of FIG. 4 illustrating one of the two pairs of wedges engaged by the threads on the stem and with the collapsible bag secured to the connecting member.

DESCRIPTION OF THE PREFERRED EMBODIMENT

Proceeding to a detailed description of a preferred embodiment of the present invention, the closure means generally 10 is shown in connection with a hollow spray stem 12 attached to a flexible bag 14 to compose a disposable douche kit. With the stem 12 removed from the bag 14 the unit can be conveniently transported in a carrying type envelope case 15. Referring specifically to FIG. 2, it will be noted that hollow spray stem or nozzle member 12 has outlet orifices 16 adjacent the outlet end and that the opposing inlet end is provided with double threaded means 18 which is formed from two continuous threads 31 and 32 which start their helixes 180° apart from the base 19 of spray stem 12.

Referring specifically to FIG. 4, it will be seen that closure means 10 is formed from an annular connecting member 11 which has an annular inner surface 20 from which extends two pairs of oppositely disposed wedges 21, 22 and 23, 24. It will be noted that wedges 21 and 22 are positioned in pairs as are wedges 23 and 24. This can better be seen in FIG. 6 showing wedges 21 and 22 adjacent the inner surface 26 of connector 11. It will be noted with reference to FIG. 5 that wedges 21 and 24, with the same being true of wedges 22 and 23, are formed on inner wall 20 in a helical pattern so as to form in effect threads for double threads 18 on nozzle 12. The arrangement of wedges 21 – 24 are such that each pair as indicated by the numerals 21, 22 and 23, 24 are located 180° from each other with wedges 21 and 22 at the same flight whereas the second pair of wedges 23 and 24 are located at another position 180° from each other and at a different flight with all wedges being positioned 90° from each other.

Referring to FIG. 6, it will be seen that spray stem or nozzle 12 has a straight wall section 28 adjacent threads 18 and a second straight wall portion 29 joining wall portion 28 at substantially a right angle to form a shoulder portion for abutment against a slightly raised ridge 30 on connecting member 11 to effect a sealing engagement between shoulder 29 and ridge 30.

Operation

A better understanding of the advantages of the closure means 10 will be had by a description of its operation. The syringe or douche unit will be carried in case 15 with the nozzle 12 removed from bag 14. When it is desired to utilize the syringe unit, the bag 14 will be filled with the appropriate fluid and nozzle 12 with thread means 18 will be inserted into connecting member 11 with threads 31 and 32 first contacting the upper pairs of wedges 23 and 24. A clockwise movement of stem 12 will then be effected so as to cause threads 31 and 32 with their associated grooves 25 to surround wedges 23 and 24 in the first instance and ultimately wedges 21 and 22 whereupon shoulder 29 is so constructed in relation to its spacing to the threads that it will contact ridge 30 to effect a tight sealing means. By means of the double helix threads 31 and 32 as well as the double flighted pairs of wedges 21, 22 and 23, 24, a quick sealing engagement is effected between the threads 31 and 32 and the wedges 21 - 24. In effect only a 180° rotation of the nozzle 12 need be accomplished in order to fully seat shoulder 29 on ridge 30 and to have the threads 18 fully surrounding all of the wedges. By having four of the wedges spaced 90° from each other and at a different flight of the helix, a fluid-tight arrangement is effected between the wedges and thread means 18 when shoulder 29 seats on ridge 30. The total combined length of the wedges is no more than 50% of the internal diameter of annular surface 20. This affords inexpensive and fast molding procedures. With the types of threads 31 and 32 and connecting member 11 with wedges 21 - 24, various types of materials can be utilized to fabricate these components and still effect a fast and fluid-tight connection. For example, thermosetting materials such as high density polyethylene have been utilized as well as semirigid yet pliable thermosetting materials such as vinyls.

While double threads 31, 32 and wedges 21 - 24 have been illustrated as being employed in conjunction with stem 12 and connector 11, respectively, it should be understood that the threads 31, 32 could be fabricated on connector 11 and wedges 21 - 24 on stem 12, and still accomplish the advantages of a fast and fluid-tight connection. In the instance where the wedges are placed on the nozzle, their total arcuate length will not exceed 50% of the circumference of the nozzle. Although not necessary with the closure means of this invention, if desired a rubber washer could be employed between shoulder 29 on stem 12 and ridge 30 on connecting member 11 to assure a fluid-tight connection.

It will thus be seen that through the present invention there is now provided a rapid and fluid-tight connection between a nozzle member and a source of fluid under pressure. The closure means can be easily molded without any special molding techniques yet requires a minimum of internal molding in a connecting member which engages the threads on the nozzle. A minimum of rotation is required to fully seat the nozzle member in a fluid-tight arrangement in the connecting member so as to result in a fluid-tight closure means.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

We claim:

1. A rapid closure means for a syringe douche kit comprising: a first hollow nozzle member defining a hollow spray stem having an annular inlet and an outlet end, a connecting member attached to a flexible bag, said connecting member presenting an annular inner surface for receiving a portion of said nozzle, in one instance said nozzle having a double threaded means and said connecting member having at least two pairs of wedges disposed in a helical pattern and spaced at at least four different positions on said annular inner surface, and in another instance said nozzle having at least two pairs of wedges disposed in a helical pattern and spaced at at least four different positions on said nozzle and said connecting member haing a double threaded means, said wedges having an arcuate length that extends no more than about 50% of the annular inlet of said nozzle or said annular inner surface of said connecting member, said double threaded means or said wedges disposed externally of and adjacent to said inlet of said hollow nozzle member when disposed thereon, said double threaded means defined by two oppositely positioned helixes having the same angle of inclination, and sealing means operatively positioned between said nozzle member and said connecting member for contact therebetween, whereby upon engagement of said wedges by said double threaded means the nozzle member can be securely fastened in said connecting member with a minimum of effort and rotation.

2. The closure means as defined in claim 1 wherein said double threaded means is carried by said nozzle member and said wedges are carried by said connecting member.

3. The closure means as defined in claim 1 wherein one pair of wedges is located 180° from each other and at the same flight of the helix and a second pair of wedges is located at another position 180° from each other and at a different flight than said first pair of wedges, with each of the wedges being located 90° from each other.

4. The closure means as defined in claim 1 wherein said nozzle member and said connecting member are formed from a thermosetting plastic material.

5. The closure means as defined in claim 2 wherein one of said pairs of wedges is positioned adjacent the surface of said connecting member opposite the nozzle member.

6. The closure means as defined in claim 2 wherein said nozzle member adjacent said double threaded means has a straight walled section joining another straight walled portion at substantially a right angle to form a shoulder portion for abutment against said connecting member.

7. The closure means as defined in claim 2 wherein said double threaded means disposed on said nozzle member is formed from two continuous threads.

* * * * *